US012788571B2

(12) United States Patent
Ciemniewska-Gorzela et al.

(10) Patent No.: US 12,788,571 B2
(45) Date of Patent: Nov. 10, 2026

(54) COLLAGEN MENISCUS CAP AND A METHOD FOR THE PRODUCTION OF A COLLAGEN MENISCUS CAP

(71) Applicants: Kinga Ciemniewska-Gorzela, Poznan (PL); Marcin Chyła, Kazmierz (PL); Maciej Cybulski, Tarnowo Podgorne (PL)

(72) Inventors: Kinga Ciemniewska-Gorzela, Poznan (PL); Marcin Chyła, Kazmierz (PL); Maciej Cybulski, Tarnowo Podgorne (PL)

(73) Assignee: MENISCUSCAP SP. Z O.O., Poznan (PL)

( * ) Notice: Subject to any disclaimer, the term of this patent is extended or adjusted under 35 U.S.C. 154(b) by 633 days.

(21) Appl. No.: 18/248,735

(22) PCT Filed: Dec. 29, 2020

(86) PCT No.: PCT/PL2020/000101
§ 371 (c)(1),
(2) Date: Apr. 12, 2023

(87) PCT Pub. No.: WO2022/081028
PCT Pub. Date: Apr. 21, 2022

(65) Prior Publication Data
US 2023/0414371 A1 Dec. 28, 2023

(30) Foreign Application Priority Data
Oct. 14, 2020 (PL) ........................................ 435677

(51) Int. Cl.

| | |
|---|---|
| ***A61F 2/38*** | (2006.01) |
| ***A61F 2/30*** | (2006.01) |
| ***A61L 27/24*** | (2006.01) |

(52) U.S. Cl.
CPC ............ *A61F 2/3872* (2013.01); *A61L 27/24* (2013.01); *A61F 2002/30062* (2013.01);
(Continued)

(58) Field of Classification Search
CPC ................ A61F 2/30756; A61F 2/3872; A61F 2002/30757; A61F 2002/3096; A61F 2002/30985; A61L 2430/06
See application file for complete search history.

(56) References Cited

U.S. PATENT DOCUMENTS 4,919,667 A * 4/1990 Richmond ............ A61F 2/3872 623/905
2003/0036797 A1 2/2003 Malaviya et al.
(Continued)

FOREIGN PATENT DOCUMENTS

CN 106693060 A 5/2017
CN 107669373 A 2/2018
(Continued)

OTHER PUBLICATIONS

Polish search report for P.435677 filed Oct. 14, 2020.
International search report for application No. PCT/PL2020/000101 mailed on Jun. 17, 2021.

*Primary Examiner* — Javier G Blanco
(74) *Attorney, Agent, or Firm* — Dennemeyer & Associates LLC

(57) ABSTRACT

A collagen meniscus cap, for the covering of a human meniscus and a method for producing a collagen meniscus cap are disclosed.

The collagen meniscus cap is formed by a set of two plates in the shape of lateral or medial meniscus, each in the form
(Continued)

of a layer of collagen membrane, placed on a bracing polymer skeleton, connected by a flexible hinge
The method of production consists of material being used to create two polymer skeletons with the shape of the lateral or medial meniscus and its reflection, connecting the polymer with collagen membrane, then the connected plates are folded together so that their inner edges overlap and collagen membranes are placed thereon. Then a tissue glue is used to cover the edges of the inner curvature 4 of both plates and the inner edges are glued together to create a hinge of the collagen meniscus cap.

1 Claim, 3 Drawing Sheets

(52) U.S. Cl.
CPC ............... *A61F 2002/30757* (2013.01); *A61F 2002/3096* (2013.01); *A61F 2002/30985* (2013.01); *A61L 2430/06* (2013.01)

(56) References Cited

U.S. PATENT DOCUMENTS

| | | | | |
|---|---|---|---|---|
| 2003/0078617 | A1 | 4/2003 | Schwartz et al. | |
| 2008/0097605 | A1 * | 4/2008 | Pastorello | A61L 27/34 128/898 |
| 2015/0238318 | A1 * | 8/2015 | McCullen | A61F 2/3872 623/14.12 |
| 2019/0314552 | A1 | 10/2019 | Wadsworth et al. | |
| 2019/0380838 | A1 | 12/2019 | Ghodbane et al. | |
| 2020/0179121 | A1 * | 6/2020 | O'Cearbhaill | A61L 27/56 |

FOREIGN PATENT DOCUMENTS

| | | | | |
|---|---|---|---|---|
| CN | 209966667 | U * | 1/2020 | |
| WO | 2006064025 | A2 | 6/2006 | |
| WO | 2012083366 | A1 | 6/2012 | |
| WO | 2012095428 | A1 | 7/2012 | |
| WO | WO-2018148722 | A1 * | 8/2018 | A61F 2/30965 |

* cited by examiner

COLLAGEN MENISCUS CAP AND A METHOD FOR THE PRODUCTION OF A COLLAGEN MENISCUS CAP

The subject of the invention is a collagen meniscus cap, in particular for the covering of a human meniscus and a method for obtaining a collagen meniscus cap. The collagen meniscus cap is used in orthopaedics for the treatment of meniscuses in humans and in veterinary medicine for the treatment of meniscus injuries in animals.

The important part played by the meniscus in the knee is commonly understood. International orthopaedics associations recommend treatment algorithms intended to save the meniscus. A simple suturing of the meniscus using various devices and materials (threads) is the best known surgical technique for meniscus repair, but it has limited indications. The best results may be obtained by suturing the meniscuses if the damage is located in the red/red or red/white blood supply zones of the meniscus and are not accompanied by degenerative changes. In the last years an increasing tendency to expand indications for the suturing of the meniscus can be observed. Biological factors which improve regeneration and healing of tissue are frequently a part of these procedures. Various strategies for biologically supporting the healing of meniscus have been developed during the last 20 years. One of these strategies is the method of suturing the meniscus and wrapping the repair site with collagen membrane (U.S. Pat. No. 8,354,119; patent date 2013 Jan. 15 Assignee: E D. Geistlich Soehne A G Fuer Chemische Industrie). The method was patented under the No 20090186062 (patent date 2009 Jan. 23 Applicant: ED. GEISTLICH SOEHNE AG FUER CHEMISCHE INDUSTRIE). The first results were satisfactory, but the technique was difficult to recreate by other surgeons. In 2010 T. Piontek et al. have created a new arthroscopic technique consisting of placing a suture on the damaged meniscus, and then wrapping it with the aforementioned collagen membrane and feeding bone marrow aspirate between the collagen membrane and the meniscus. The results of 2 and 5-year follow-up of the treatment have demonstrated that the technique is safe and that additional tools may be used for the repair of meniscus in patients for whom the removal of the meniscus was planned otherwise. The technique is however complicated, and the material in the form of collagen membrane does not provide sufficient early post-operative stabilisation of meniscus injury. A new implant is needed, which will be easy to place over the damaged meniscus in arthroscopic technique. It will form a scaffolding for cells which enable the regeneration processes of the injured meniscus, giving a chance to obtain a future effect of healed meniscus with its functionality returned. This implant will mechanically stabilise the fragments of injured meniscus right after the surgery, enabling early rehabilitation.

The essence of the invention is a collagen meniscus cap, which is formed by a set of two plates in the shape of lateral or medial meniscus, each in the form of a layer of collagen membrane, placed on a bracing polymer skeleton, connected by a flexible hinge, whereas the thickness of the collagen membrane is within the range of H (0.4-0.9) mm, advantageously 0.6 mm, and the thickness of the polymer layer is within the range of h (0.2-0.6) mm, advantageously 0.45 mm, and the polymer skeleton has the shape of intersecting segments which form a mesh.

A method for the production of a collagen meniscus cap consists of bio-absorbable and/or bio-degradable material being used to create, advantageously in a 3D technology by printing directly over collagen membrane, two polymer skeletons with the shape of the lateral or medial meniscus and its mirror reflection, permanently connecting the polymer with collagen membrane, after which the connected plates are cut until the shape of the lateral or medial meniscus, advantageously with a guillotine, then the cut collagen membrane plates are folded together so that the inner edges of the plates overlap and collagen membranes are placed on each other, then a tissue glue is used to cover the edges of the inner curvature of both plates of the collagen membrane to the inner outline of the polymer printout, and in turn the inner edges are glued together to create a hinge of the collagen meniscus cap, after which the set is dried in ambient temperature to obtain the effect of gluing together.

The use of the solution presented in the invention enables the following technical and utility effects:

- the shape of the meniscus cap and its permanent structure the moment of implantation facilitates the surgery,
- the polymer skeleton containing polyurethane forms additional mechanical stabilisation of the damaged fragments of the meniscus, increasing the "mechanical calm", with an advantageous impact on the healing processes,
- the permanent shape of the cap enables the restoration of the correct shape of the meniscus after its damage and degeneration,
- the used collagen membrane is a site where cells readily implant and take part in the process of reconstruction and regeneration of the meniscus,
- the collagen membrane with polymer skeleton increases the volume of the meniscus, which is significant in particular during the treatment of degenerative injuries in which we observe a reduction of the meniscus volume,
- for the manufacturing of the meniscus cap existing products with proven safety of use in humans and animals.

The subject of the invention in an example, but not limiting implementation is presented on the drawing figures.

BRIEF DESCRIPTION OF THE DRAWINGS

FIG. 2 shows the meniscus cap in a cross-section in a plane perpendicular to the cap's surface, and.

Figure 1:
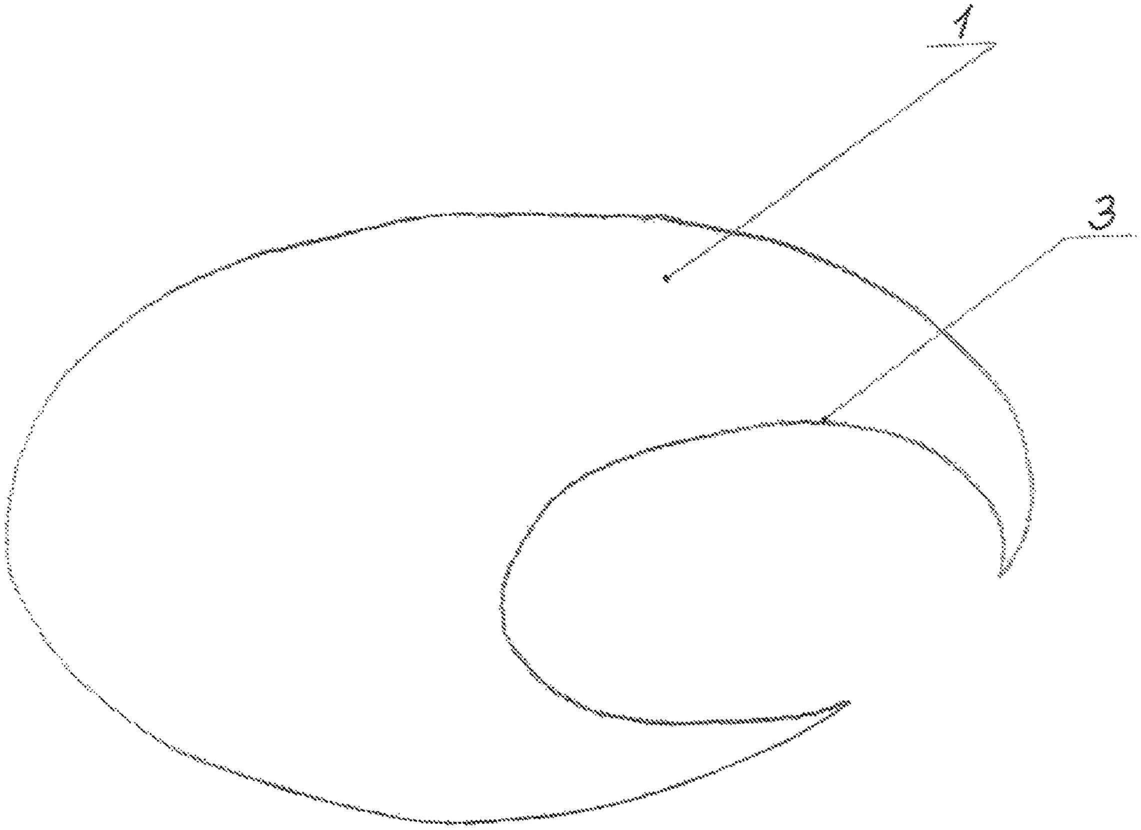
FIG. 1 shows the cap in a top view presenting the shape of the cap similar to the shape of the medial meniscus of the knee.
Figure 2:
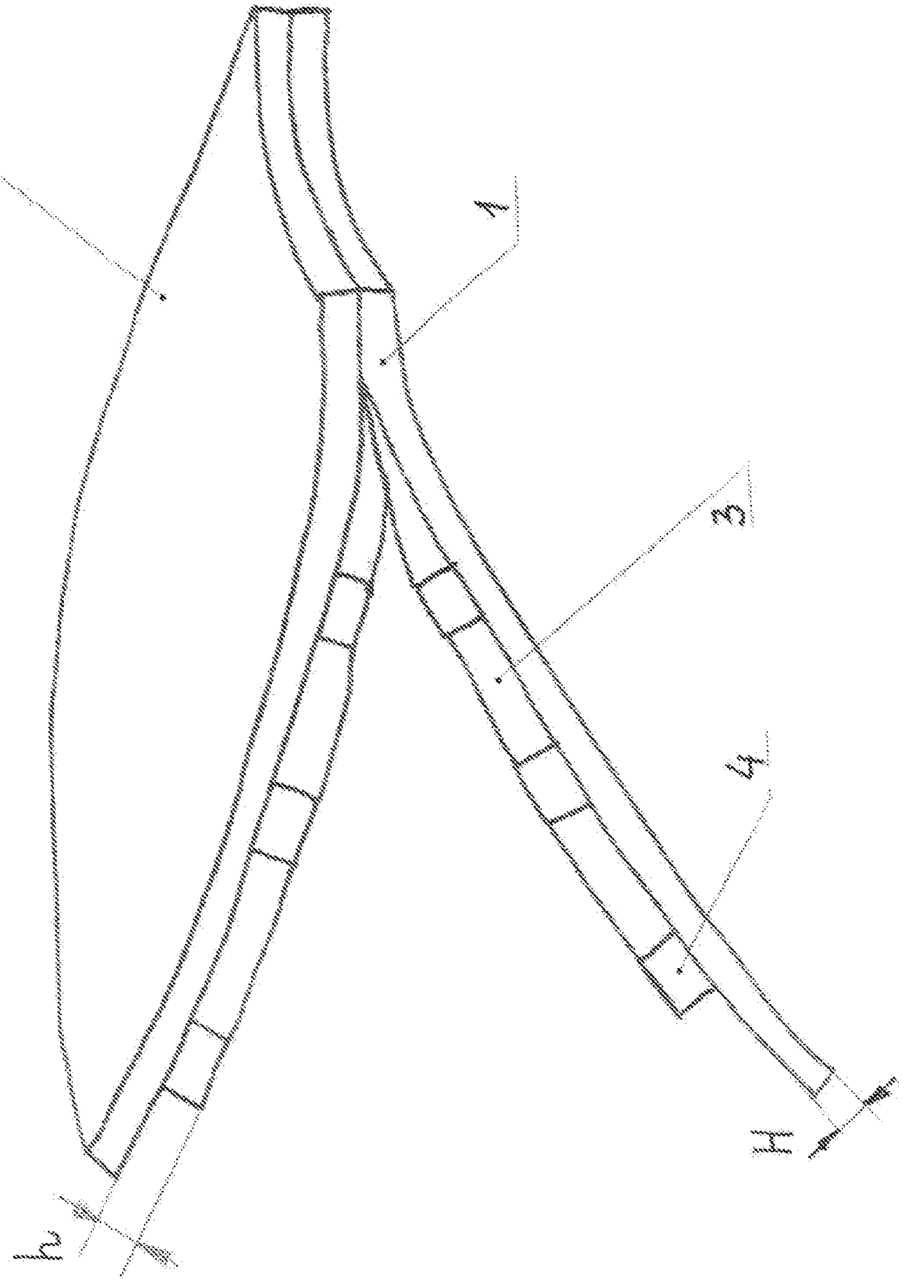
Figure 3:
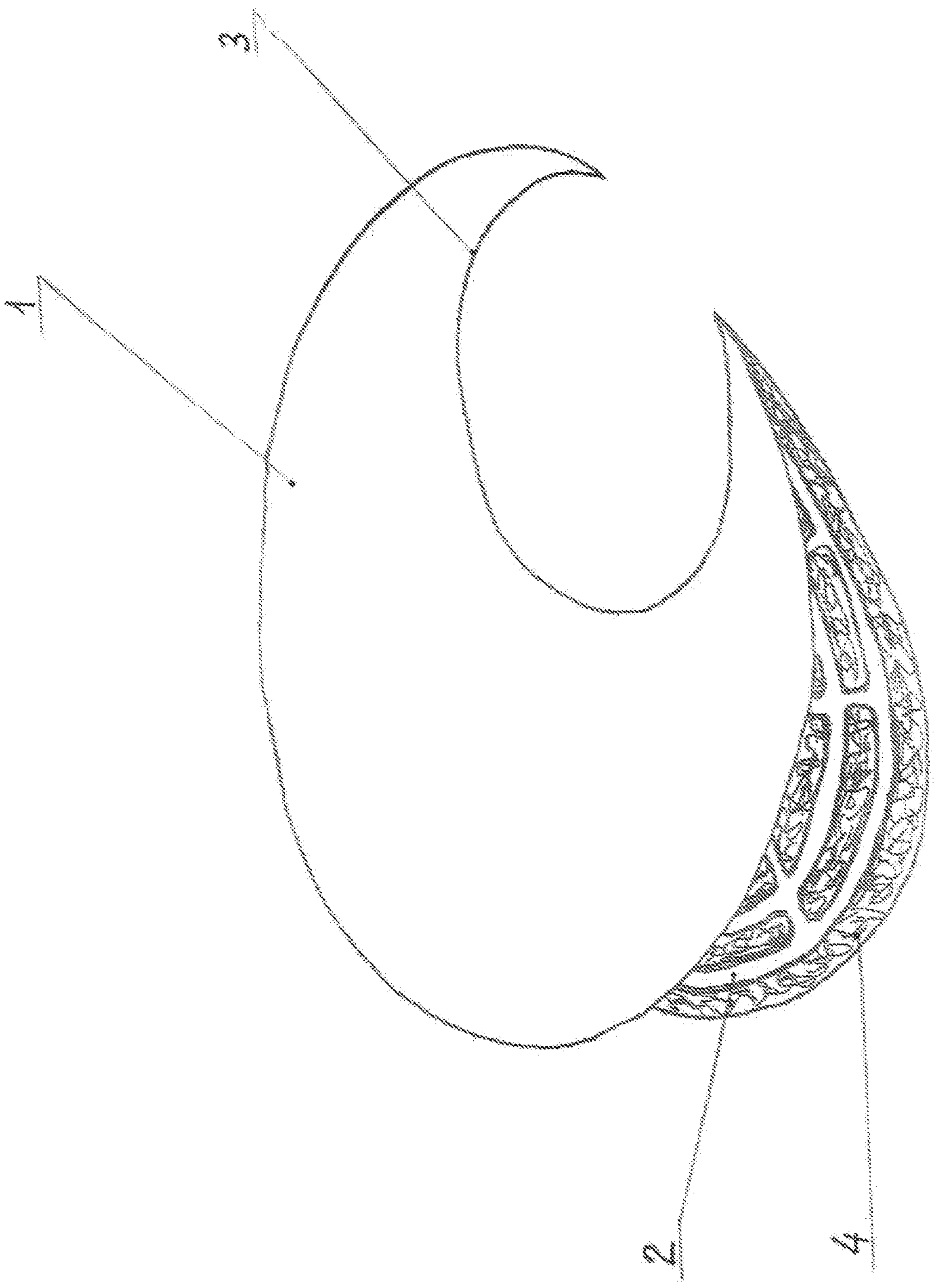
FIG. 3 shows the meniscus cap in an oblique projection visible in its entirety.

The collagen meniscus cap is formed by a set of two plates 1 in the shape of lateral or medial meniscus, each in the form of a layer of collagen membrane, placed on a bracing polymer skeleton 2, connected by a flexible hinge 3. The thickness of the collagen membrane is within the range of H (0.4-0.9) mm, advantageously 0.6 mm, and the thickness of the polymer layer is within the range of h (0.2-0.6) mm, advantageously 0.45 mm. The polymer skeleton 2 has the shape of intersecting segments which form a mesh.

A method for the production of a collagen meniscus cap consists of bio-absorbable and/or bio-degradable material being used to create, advantageously in a 3D technology by printing directly over collagen membrane, two polymer skeletons 2 with the shape of the lateral or medial meniscus and its mirror reflection, permanently connecting the polymer with collagen membrane. Afterwards the connected plates 1 are cut until the shape of the lateral or medial meniscus, advantageously with a guillotine. Then the cut collagen membrane plates 1 are folded together so that the inner edges of the plates 1 overlap and collagen membranes are placed on each other. Then a tissue glue is used to cover the edges of the inner curvature 4 of both plates 1 of the collagen membrane to the inner outline of the polymer skeleton 2 printout. The next stage is gluing together the inner edges to create a hinge 3 of the meniscus cap. In the last stage the set is dried in ambient temperature to obtain the effect of gluing together After anesthetising the patient an Esmarch tourniquet is placed on the thigh of the operated limb in order to perform the surgery in ischaemic conditions. Subsequently typical surgical approaches are made, anterolateral and anteromedial (horizontal incision) to the knee joint, after which diagnostic arthroscopy of the knee joint is performed. After establishing a complex injury of the meniscus, sutures are placed which stabilise the damaged fragments of the meniscus, after which the size of the defect is measured in order to fit the meniscus cap. After removing from a sterile packaging, the meniscus cap is cut down appropriately, then an appropriate access to the lateral or median compartment is enlarged and an unobstructed passage through the soft tissues around the joint is created. Then the meniscus cap is introduced into the joint using a surgical tool, e.g. a pean. Afterwards the injury site is covered by the meniscus cap, which is stabilised on the meniscus using meniscal sutures.

Another activity is the aspiration of bone marrow from the intercondylar incision of the operated knee, which is then fed into the space between the meniscus and the meniscus cap under the conditions of dry arthroscopy. Afterwards layered suture is used to close the wound, a sterile dressing is applied and the Esmarch tourniquet is released, which ends the surgery.

Postoperative procedure and rehabilitation is conducted in accordance with the protocol for the suturing of the meniscus with the use of collagen membrane.

The invention claimed is:

1. A method for the production of a collagen meniscus cap comprising the steps of:

using bio-absorbable and/or bio-degradable material to create, by 3D printing directly over a collagen membrane, two polymer skeletons (2) with the shape of the lateral or medial meniscus and its mirror reflection;

permanently connecting each of the polymer skeletons (2) with the collagen membrane to form two plates (1);

cutting the connected plates (1) until they form the shape of the lateral or medial meniscus, wherein each plate (1) comprises a polymer skeleton (2) placed on a layer of collagen membrane;

folding the cut plates (1) together so that inner edges of the two plates (1) overlap and the layers of collagen membrane of the two plates are placed against each other;

applying a tissue glue to cover the edges of an inner curvature (4) of both plates (1) to an inner outline of the polymer skeletons (2); and gluing the inner edges together to create a hinge (3) of the collagen meniscus cap, after which the assembly is dried at ambient temperature to obtain the effect of bonding, wherein each of the two polymer skeletons (2) defines a mesh of intersecting segments, wherein the collagen meniscus cap is sized and configured to be placed over a damaged meniscus of a knee.

* * * * *